(12) United States Patent
Sagawa et al.

(10) Patent No.: US 8,025,779 B2
(45) Date of Patent: Sep. 27, 2011

(54) WATER QUALITY ANALYZER

(75) Inventors: Kiyoshi Sagawa, Tokyo (JP); Shinichi Harima, Daisen (JP); Kazuo Onaga, Osaka (JP); Junko Yanagitani, Itami (JP); Osamu Inazawa, Itami (JP)

(73) Assignees: Tanita Corporation, Tokyo (JP); FIS Inc., Itami-shi (JP)

( * ) Notice: Subject to any disclaimer, the term of this patent is extended or adjusted under 35 U.S.C. 154(b) by 1417 days.

(21) Appl. No.: 10/578,442

(22) PCT Filed: Nov. 10, 2004

(86) PCT No.: PCT/JP2004/016638
§ 371 (c)(1),
(2), (4) Date: May 5, 2006

(87) PCT Pub. No.: WO2005/047880
PCT Pub. Date: May 26, 2005

(65) Prior Publication Data
US 2007/0084722 A1 Apr. 19, 2007

(30) Foreign Application Priority Data

Nov. 14, 2003 (JP) .................. 2003-385600
Feb. 20, 2004 (WO) .................. PCT/JP2004/002029

(51) Int. Cl.
*G01N 33/487* (2006.01)
*G01N 27/26* (2006.01)

(52) U.S. Cl. ........ 204/400; 205/789; 205/743; 205/775; 210/93; 210/743; 210/746; 702/22; 702/100; 204/416; 204/433; 436/125

(58) Field of Classification Search .......... 205/400–435, 205/789, 743, 775; 702/25, 22, 100; 324/694, 324/439, 464; 210/85, 93, 743, 746; 250/281; 204/400–435; 436/125
See application file for complete search history.

(56) References Cited

U.S. PATENT DOCUMENTS
4,227,974 A * 10/1980 Petersen et al. ............ 205/779.5
(Continued)

FOREIGN PATENT DOCUMENTS
JP 57-172244 10/1982
(Continued)

OTHER PUBLICATIONS
Japanese Office Action dated Jun. 29, 2004.
(Continued)

*Primary Examiner* — Jeffrey T Barton
*Assistant Examiner* — Jennifer Dieterle
(74) *Attorney, Agent, or Firm* — Edwards Angell Palmer & Dodge LLP

(57) ABSTRACT

A water quality analyzer comprises: sensor electrodes $1a$, $1b$ made of different metals from each other, the electrodes in a liquid of inspecting object generating a sense voltage in proportion to the liquid's impurities concentration; an operational amplifier OP1 amplifying the sense voltage without inverting to provide for a CPU 3; a resistor R0 whose one end is connected to the electrode $1a$; and a voltage divider 2 applying a voltage obtained by dividing the sense voltage by a prescribed division ratio to R0's another end. The CPU 3 calculates input signal from OP1 to obtain chlorine concentration and displays the calculated result on a LCD 4 in a measurement mode, and sets the division ratio of the divider 2 so that sense voltage across electrodes $1a$, $1b$ soaked in a liquid including prescribed concentration chloride approximately agrees with a reference voltage of prescribed concentration in a sense-voltage calibration mode.

9 Claims, 12 Drawing Sheets

U.S. PATENT DOCUMENTS

| | | | |
|---|---|---|---|
| 5,346,605 A * | 9/1994 | Wolcott et al. | 204/412 |
| 6,054,030 A * | 4/2000 | Pierangela et al. | 204/404 |
| 6,653,842 B2 * | 11/2003 | Mosley et al. | 324/446 |

FOREIGN PATENT DOCUMENTS

| | | |
|---|---|---|
| JP | 62-153740 A | 7/1987 |
| JP | 02-115756 A | 4/1990 |
| JP | 6-201649 | 7/1994 |
| JP | 06-506060 A | 7/1994 |
| JP | 08-500444 A | 1/1996 |
| JP | 8-136501 | 5/1996 |
| JP | 10-82761 | 3/1998 |
| JP | 2002-214220 | 7/2002 |
| WO | WO-9217775 A1 | 10/1992 |

OTHER PUBLICATIONS

Notification of Reasons for Refusal dated Oct. 5, 2010, for Japanese Patent Application No. JP 2005-515430.

\* cited by examiner

WATER QUALITY ANALYZER

TECHNICAL FIELD

The invention relates to water quality analyzers that are preferably used to measure water quality of a liquid of sensing object and more particularly to measure concentration of residual chlorine included in tap water, or dissolved ozone, dissolved oxygen, dissolved hydrogen, dissolved carbon dioxide in the liquid.

BACKGROUND ART

A water quality analyzer for measuring residual chlorine concentration in tap water is disclosed in Japanese Laid-open Patent Publication No. 2002-214220. The water quality analyzer has a pair of electrodes made of different metals and inspects chlorine concentration in a liquid of inspecting object from an electromotive voltage generated across the electrodes with the electrodes soaked in the liquid. One of the electrodes is made of platinum wire, while the other is made of silver wire and has silver chloride coat at its part soaked in the liquid. The pair of electrodes constitute a sensor. When the sensor is soaked in a liquid of inspecting object, for example, tap water, an electromotive voltage is generated across the pair of electrodes in response to chlorine concentration in the liquid.

Thus, chlorine concentration in a liquid of inspecting object is measured based on an electromotive voltage generated across the pair of electrodes when the electrodes is soaked in the liquid. However, detection precision of the chlorine concentration was low due to large dispersion in the electromotive voltages among those individual sensors. FIG. 18a shows electromotive voltages of sensors that are soaked in a liquid (clean water) with chlorine concentration of 0% and liquids (tap water) with 0.4 ppm (residual chlorine concentration), 0.9 ppm and 1.5 ppm. There was a tendency that the electromotive voltages saturated in high concentration side, and also dispersion in the electromotive voltages was large among the sensors. For example, the chlorine concentration generating the electromotive voltage of 325 mV disperses between 0.6 ppm and 1.5 ppm (see d1 in FIG. 18a).

It is considered that such dispersion in the electromotive voltages is brought by factors such as crack occurred in silver chloride coat on the one electrode surface or the like. FIG. 17 is an equivalent circuit diagram of a sensor 1 comprised of the pair of electrodes. The inventors considered that a voltage source E generating an electromotive voltage was connected in parallel with an impedance element Z2 by crack occurred in the silver chloride coat or the like, so that the dispersion in the electromotive voltages was brought by dispersion among individual sensors in an impedance value of the impedance element Z2. Incidentally, Z1 in FIG. 17 is an internal impedance of the sensor.

In this way, while electromotive voltages generated across the electrodes have dispersion among individual sensors, the dispersion in the electromotive voltages is remarkable in high concentration side and an inclination of the electromotive voltages is substantially the same among the sensors. Accordingly, when a constant voltage is added to or subtracted from electromotive voltages of each sensor in a range of high concentration side so that the electromotive voltage of the sensor soaked in a liquid of, for example, 0.4 ppm becomes a prescribed reference voltage (e.g., 200 mV), it is possible to calibrate electromotive voltages of each sensor. However, in this calibration technique (hereinafter referred to as a shift calibration), effect on reduction of the dispersion in the electromotive voltages was insufficient. FIG. 18b shows electromotive voltages after the shift calibration. Since chlorine concentration generating, for example, the electromotive voltage of 325 mV has dispersion between 0.8 ppm and 1.55 ppm (d2 in FIG. 18b), further improvement of inspection precision is required.

It was also not possible to detect water quality of a liquid of inspecting object at high precision since linearity of electromotive voltages generated across the electrodes was deteriorated by the tendency that the electromotive voltages saturated in high concentration side, as mentioned above.

DISCLOSURE OF THE INVENTION

The present invention is provided in view of issues described above, and an object is to provide a water quality analyzer that can detect water quality of a liquid of inspecting object at high precision.

By the way, it is supposed that the above dispersion in the electromotive voltages is brought by the dispersion among individual sensors in the impedance value of the impedance element Z2 which is created by factors such as the crack occurred in the silver chloride coat on the one electrode or the like and is connected in parallel with the voltage source E. For that reason, the inventors thought that, as shown in FIG. 4a, the dispersion in the electromotive voltages could be reduced by: connecting a pair of sensor electrodes in parallel with an impedance element Z3 having a variable-resistance value; and adjusting an impedance value of the impedance element Z3 so that an output voltage V1 across the sensor electrodes soaked in a liquid including chlorine of a prescribed concentration agrees with a reference voltage in the prescribed concentration.

Namely, a water quality analyzer according to the present invention comprises the following configuration.

A pair of sensor electrodes that are made of different metals from each other and are soaked in water and used, wherein the sensor electrodes generate a sense voltage across the electrodes in proportion to concentration of impurities included in the water;

a detection means that detects concentration of solute from a voltage value of the sense voltage to provide a detection result; and an impedance adjustment means that adjusts an input impedance across both ends of the sensor electrodes so that with the sensor electrodes soaked in a liquid of reference concentration, the sense voltage generated across the sensor electrodes agrees with a reference voltage corresponding to the above reference concentration.

Therefore, since the water quality analyzer of the invention adjusts the input impedance across the sensor electrodes through the impedance adjustment means so that the sense voltage generated across the sensor electrodes substantially agrees with the reference voltage with the pair of sensor electrodes soaked in the liquid of reference concentration, it is possible to correct dispersion in an output impedance across the sensor electrodes to reduce dispersion in electromotive voltages generated across the sensor electrodes and improve sense precision of the concentration of solute.

Now, when a circuit is considered, in which as shown in FIG. 4b one end of a resistor R0 is connected to an electrode of the positive side of an electromotive voltage V1 generated across the pair of electrodes and also another end of the resistor R0 is connected to a center tap of a variable resistor VR across which the electromotive voltage V1 generated across the electrodes is applied, a voltage V2 obtained by dividing the electromotive voltage V1 by a prescribed division ratio is applied to the another end of the resistor R0. It is thought that it is possible to adjust an impedance value (comprised of resistor R0 and variable resistor VR) of an impedance element Z3 connected between the electrodes by adjusting the voltage V2 since the voltage V2 applied to the another end of the resistor R0 is changed by adjusting a resistance value of the variable resistor VR and then a voltage applied across the resistor R0 is changed.

Then, it is also preferable that the above impedance adjustment means comprises: a resistor and a voltage divider that are connected in series between both ends of the sensor electrodes; and a division ratio controlling means that controls a division ratio of the voltage divider. The voltage divider generates a divided voltage obtained by dividing the sense voltage generated across the sensor electrodes by the division ratio set through the division ratio controlling means, and then applies a differential voltage between the sense voltage and the divided voltage across the above resistor. The division ratio controlling means provides a calibration mode of the sense voltage and sets so that the sense voltage in the above reference concentration agrees with the above reference voltage in the calibration mode. Since the differential voltage between the sense voltage and the divided voltage of the voltage divider is applied across the resistor that is connected between the sensor electrodes through the voltage divider, the division ratio controlling means can adjust the input impedance including the resistor between the sensor electrodes by adjusting the division ratio of the voltage divider to adjust a voltage applied across the resistor.

It is also preferable that the above voltage divider comprises: a first and a second voltage dividing resistors that divide the above sense voltage; and a series circuit of an adjustment resistor and a switch means. The above series circuit is connected between both ends of at least any one of the voltage dividing resistors. The above division ratio controlling means changes the division ratio by turning on/off the above switch means. It is possible to change the division ratio of the voltage divider in ways.

Another water quality analyzer according to the present invention comprises the following configuration.

A pair of sensor electrodes that are made of different metals from each other and are soaked in water and used, wherein the sensor electrodes generate a sense voltage across the electrodes in proportion to concentration of impurities included in the water;

a detection means that detects concentration of solute from a voltage value of the sense voltage to provide a detection result; and an impedance element that is connected between the sensor electrodes, whose impedance value is a resistance value that can improve non-linearity of the sense voltage.

Since an output impedance across the sensor electrodes is lowered through the impedance element connected between the sensor electrodes up to around the level by which the non-linearity of the sense voltage is improved, it is possible to improve sense precision of concentration of detecting object. Though a resistor is connected between the pair of sensor electrodes also in the conventional water quality analyzer described in TECHNICAL FIELD, the resistor is connected for purpose of noise reduction in order to improve a problem that the analyzer is liable to noise when an output impedance across the sensor electrodes is high. Accordingly, since the resistor had a value of 10 MΩ and was high, improvement effect of the non-linearity of the sense voltages was not obtained.

It is also preferable that the analyzer is provided with: an offset voltage supply means that superposes an offset voltage on the sense voltage; and an amplification means that amplifies a voltage obtained by superposing the offset voltage on the sense voltage at a prescribed gain to provide for the detection means. The above detection means detects the concentration of solute based on a voltage value of an input voltage from the above amplification means. The analyzer comprises a setting means that provides a calibration mode of the sense voltage and sets the offset voltage and the gain so that with the sensor electrodes soaked in a liquid of reference concentration, the sense voltage generated across the sensor electrodes agrees with a reference voltage corresponding to the above reference concentration in the calibration mode.

It is also preferable that the impedance value of the impedance element is equal to or more than 1 kΩ and equal to or less than 1 MΩ.

BEST EMBODIMENT FOR CARRYING OUT THE INVENTION

In order to describe the present invention in detail, the invention is explained in conjunction with the accompanying drawings.

First Embodiment

Figure 1:
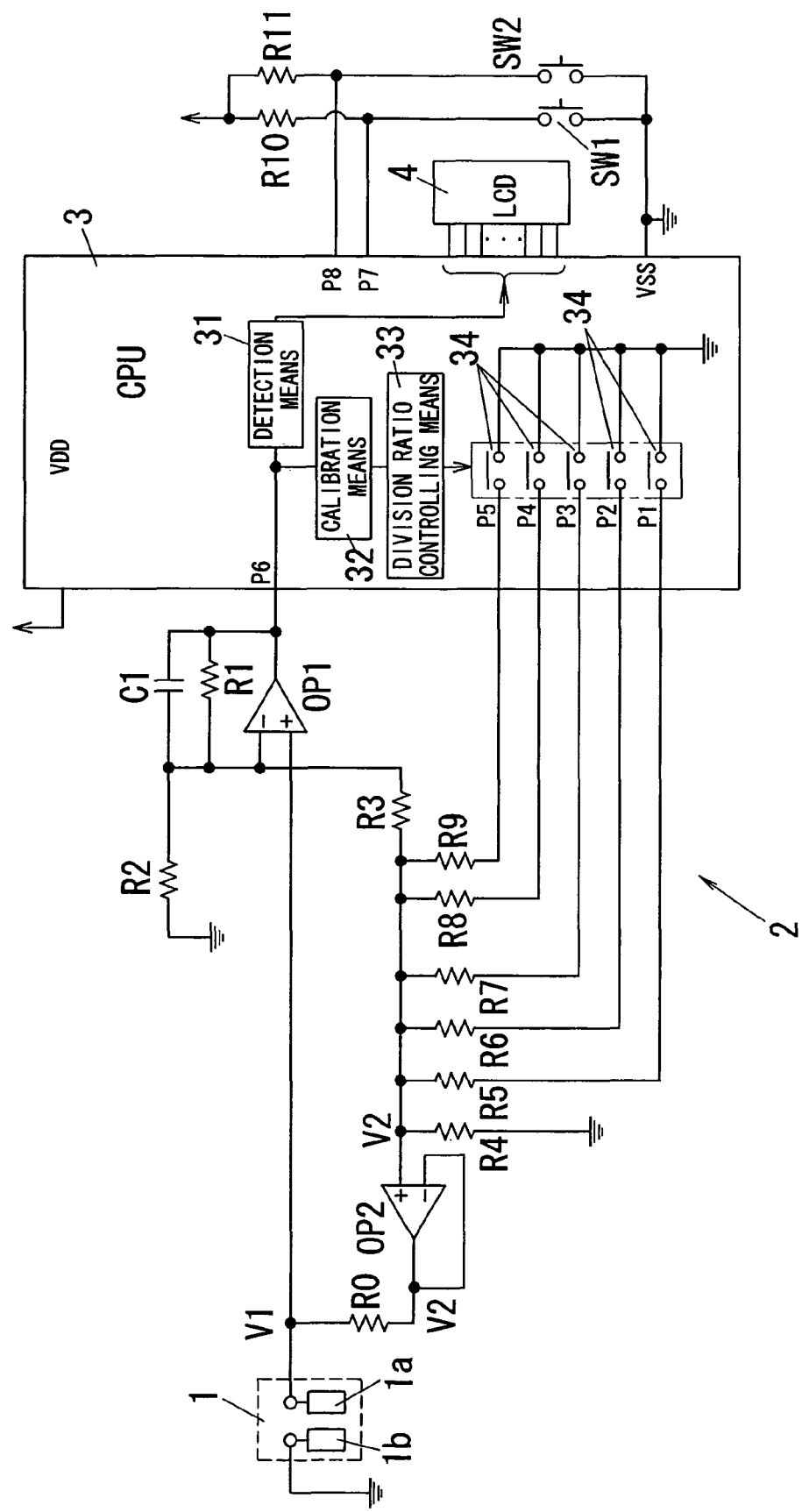
FIG. 1 is a circuit diagram of a water quality analyzer according to a first embodiment of the present invention.

FIG. 1 shows a water quality analyzer according to a first embodiment of the present invention. The water quality analyzer comprises a sensor 1, a resistor R0, a voltage divider 2 and a CPU 3. The sensor 1 is comprised of a pair of sensor electrodes 1a and 1b that are made of different metals from each other. When soaked in a liquid of inspecting object, the sensor electrodes generates a sense voltage in proportion to concentration of impurities included in the liquid. One end of the resistor R0 is connected to the sensor electrode 1a of the positive side when the pair of sensor electrodes 1a and 1b are soaked in the liquid of inspecting object (e.g., water including residual chlorine). The voltage divider 2 applies a voltage V2 to another end of the resistor R0. The voltage V2 is obtained by dividing the sense voltage V1 by a prescribed division ratio. The sensor electrode 1a of the positive side in the pair of sensor electrodes 1a and 1b is connected to a non-inverting input terminal of an operational amplifier OP1.

The operational amplifier OP1 constitutes a non-inverting amplifier. A parallel circuit comprised of a resistor R1 and a condenser C1 for adjusting response is connected between an output end and the non-inverting input end of the amplifier OP1. The gain of the amplifier OP1 is set with a resistance value of the resistor R1 and a resistance value of a resistor R2 that is connected between its inverting input end and ground. The sense voltage amplified with the operational amplifier OP1 is applied to an input terminal P6 of the CPU 3.

The voltage divider 2 is constructed with a first and a second voltage dividing resistors R3 and R4, an operational amplifier OP2, a plurality (e.g., five in the embodiment) of adjustment resistors R5-R9 and five switch means 34. The resistors R3 and R4 are connected in series between the inverting input end of the operational amplifier OP1 and ground. A non-inverting input terminal of the operational amplifier OP2 is connected to a junction point of the first and second voltage dividing resistors R3 and R4. The resistors R5-R9 are connected between the junction point of the first and second voltage dividing resistors R3 and R4 and connection terminals P1-P5 of the CPU 3, respectively. The five switch means 34 are built in the CPU 3, and connected between the adjustment resistors R5-R9 and ground, respectively. Hereupon, the operational amplifier OP2 constitutes a non-inverting amplifier of voltage follower, and applies an output voltage to the another end of the resistor R0. The output voltage is equal to an input voltage into the non-inverting input end.

The sense voltage amplified through the operational amplifier OP1 is applied to the input terminal P6 of the CPU 3, and the sense voltage is A/D-converted with a built-in A/D conversion part and then chlorine concentration is obtained through arithmetic. A detection value of the chlorine concentration is displayed on a liquid crystal display (hereinafter referred to as a LCD) 4. One ends of the adjustment resistors R5-R9 are connected to the output terminals P1-P5 of the CPU 3, and the adjustment resistor(s) R5-R9 is selectively connected in parallel with the second voltage dividing resistor R4 by individually turning on and off the switch means 34 built in the CPU 3 to connect the output terminal(s) P1-P5 to ground or change to high impedance state. Just then, since a combined impedance of the second voltage dividing resistor R4 and the resistor(s) R5-R9 is changed and the division ratio of the voltage divider 2 is changed, it is possible to change a voltage value of the voltage V2 applied across the resistor R0. Namely, a detection means 31, a division ratio setting means 33 and a calibration means 32 are constructed by an arithmetic function of the CPU 3. The means 31 detects concentration of chlorine in the liquid of inspecting object from an electromotive voltage generated across the pair of sensor electrodes 1a and 1b when the sensor electrodes 1a and 1b is soaked in the liquid. The means 33 sets the division ratio of the voltage divider 2 by turning on/off the above switch means 34. The means 32 provides a calibration mode of the sense voltage, and decides the division ratio of the voltage divider 2 and then controls the division ratio of the voltage divider 2 by selectively turning on/of the switch means 34 using the division ratio setting means 33 in the calibration mode.

An operation signal through a switch SW1 for measurement start is supplied to an input terminal P7 of the CPU 3, while an operation signal through a switch SW2 for calibration start is supplied to its input terminal P8. One ends of the switches SW1 and SW2 are connected to ground, and also their another ends are pulled up to a constant voltage through resistors R10 and R11, respectively. Accordingly, if a voltage level of the input terminal P7 or P8 is set to Low or High by turning on/off the switch SW1 or SW2 and then an operation signal is supplied to the CPU 3, the CPU 3 starts to operate in a measurement mode or a calibration mode.

Figure 2:
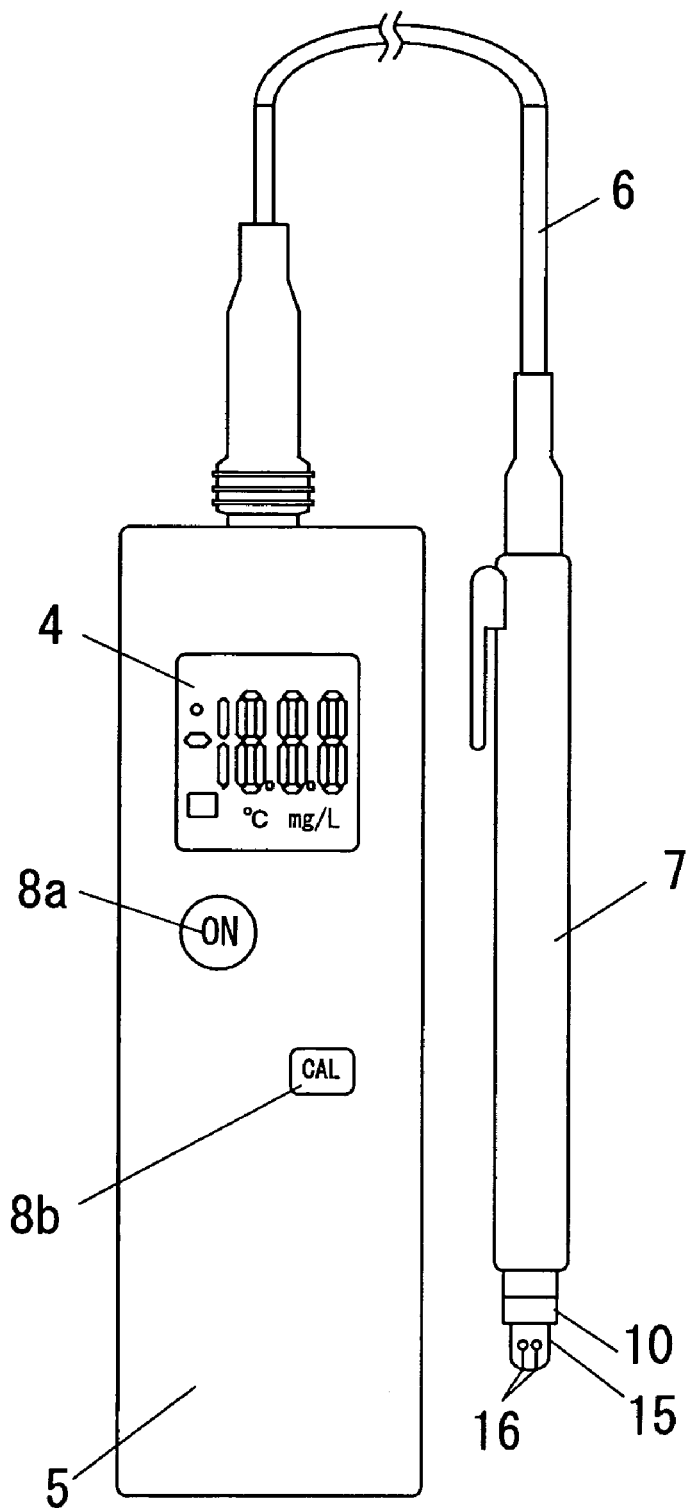
FIG. 2 is an outside drawing of the above water quality analyzer.

FIG. 2 is an outside drawing of the water quality analyzer of the embodiment, and the above circuit of FIG. 1 is enclosed in a housing 5 made of a resin molding. The housing 5 is connected with a sensor body 7 through a cable 6, and a tip of the sensor body 7 is provided with a head 10 that includes a sensor 1 comprised of the pair of the sensor electrodes 1a and 1b. The LCD 4, operating keys 8a and 8b of switch SW1 and SW2, and so on are arranged on the front of the housing 5.

Figure 3A:
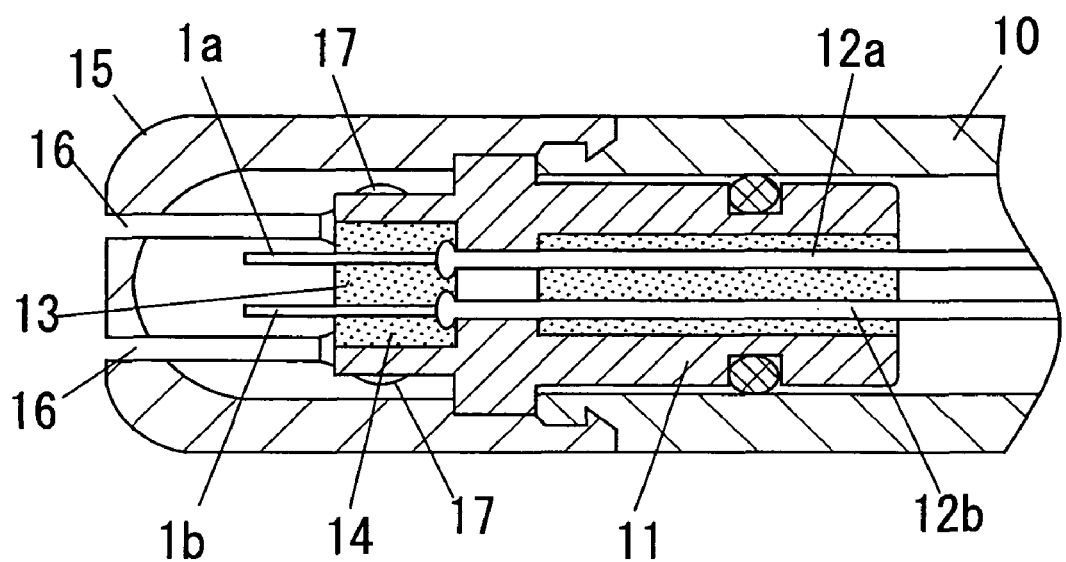
FIG. 3a is a sectional view of a major part of a head in the above water quality analyzer.
Figure 3B:
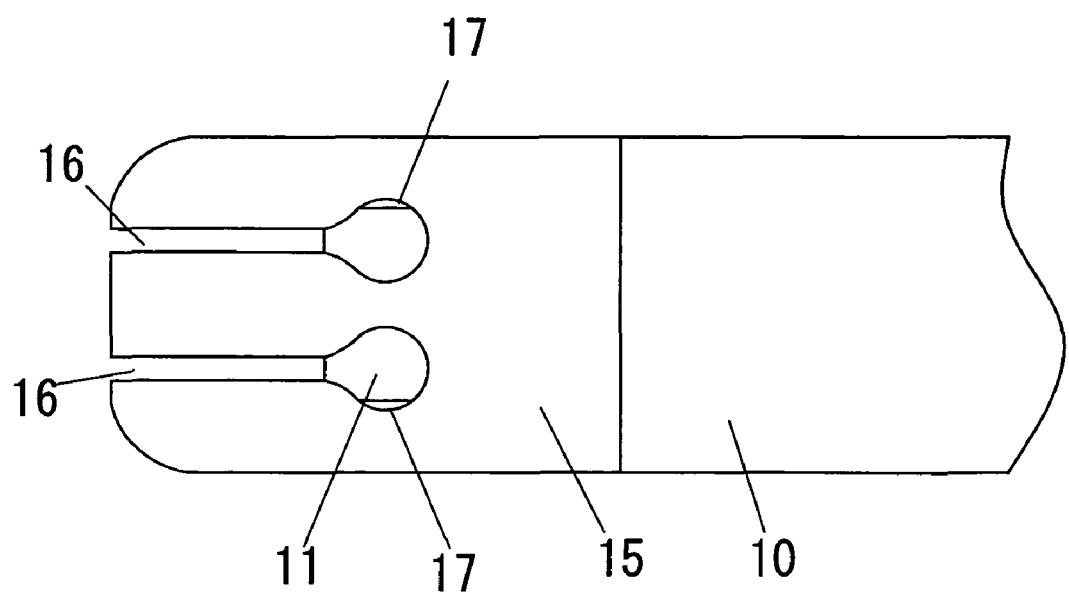
FIG. 3b is a lateral view of a major part of a head in the above water quality analyzer.
Figure 4A:
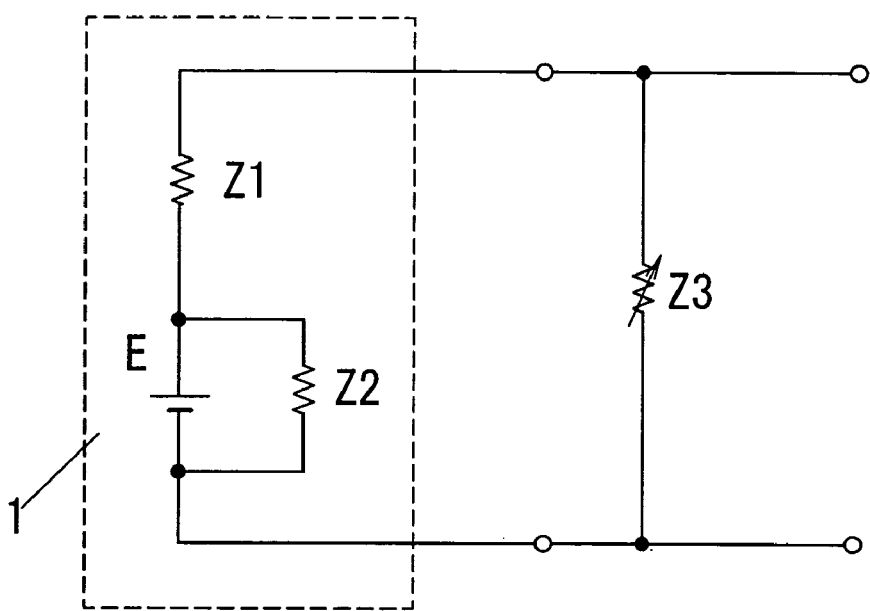
FIG. 4a is an explanatory diagram of a correction method of a sense voltage according to the same as the above.
Figure 4B:
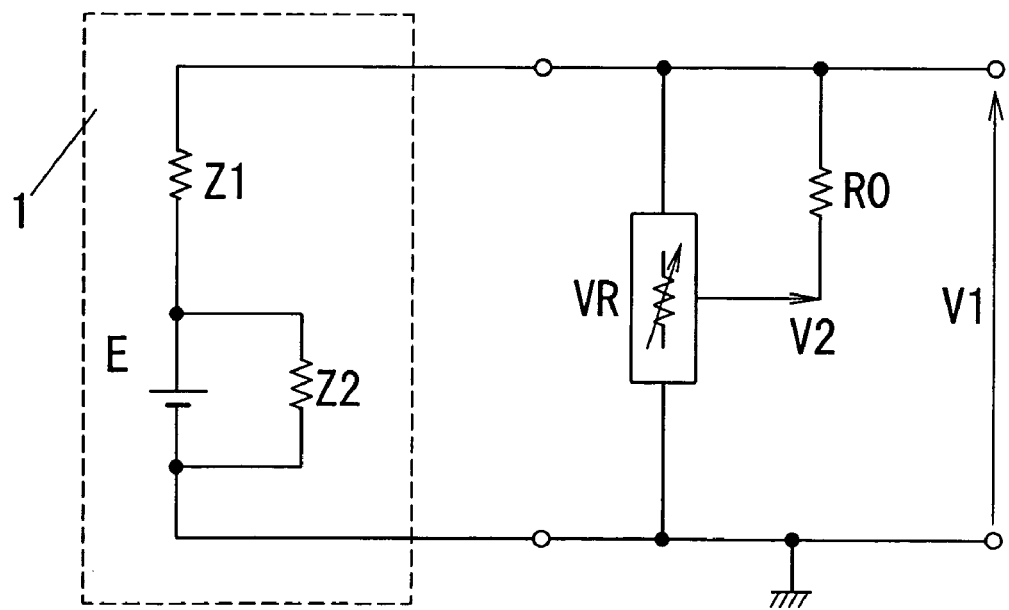
FIG. 4b is an explanatory diagram of a correction method of a sense voltage according to the same as the above.

FIG. 3a is an enlarged sectional view of the head 10 and FIG. 3b is an enlarged lateral view of the head 10. The head 10 is formed into a long and narrow cylindrical shape whose hollow is connected to the inside of the sensor body 7, and has an opening at the tip. A fix member 11 is attached to the tip of the head 10 with water-tightness inside the head 10 secured, and the pair of the sensor electrodes 1a and 1b are fixed to the fix member 11. Two lead wires 12a and 12b are located in the hollow of the head 10, while each back-end of the lead wires 12a and 12b is connected to a core wire of the cable 6 and connected to the circuit of FIG. 1 enclosed in the housing 5 through the core wire of the cable 6. Front ends of the lead wires 12a and 12b protrude in a front concavity 13 of the fix member 11 to be respectively connected to the sensor electrodes 1a and 1b, and are fixed with sealant 14 filled in the front concavity 13.

One of the sensor electrodes 1a and 1b, i.e., the sensor electrode 1b is made of platinum wire, and another sensor electrode 1a is made of silver wire. The back-end sides of the sensor electrodes 1a and 1b are formed as a buried part that is buried and fixed in the front concavity 13 of the fix member 11 with the sealant 14, while the front-end sides is formed as a sense part that protrudes forward from the sealant 14. Silver chloride coat is formed only on the surface of the above sense part of the sensor electrode 1a made of silver wire, but silver chloride coat is not formed on the surface of the buried part. Accordingly, since silver chloride coat is not formed at the junction of the sensor electrode 1a and the lead wire 12a, electrical connection of the sensor electrode 1a and the lead wire 12a is not inhibited by silver chloride coat.

A cap 15 is further attached to the tip of the head 10 so as to cover the fix member 11 and the sense part of the sensor electrodes 1a and 1b. Thereby, the sense part of the sensor electrodes 1a and 1b is protected. The cap 15 has two parallel slit-shaped openings 16 and the inside of the cap 15 is connected to the outside through the openings 16. The openings 16 are formed from a side to the opposite side along the front-end surface. At the both ends of each opening 16, the cap 15 also has connection holes 17 that are connected to the openings 16 and also connects the inside of the cap 15 and the outside. The connection hole 17 has a diameter larger than a width of each opening 16. Hereupon, the openings 16 and the connection holes 17 soak the sense part of the sensor electrodes 1a and 1b in a liquid of inspecting object such as tap water or the like by flowing the liquid inside the cap 15 when chlorine concentration in the liquid is measured, and also drains the liquid from the inside of the cap 15 after the chlorine concentration in the liquid is measured.

The operation of the water quality analyzer of the embodiment is now explained.

First, the measurement mode for measuring chlorine concentration in a liquid of inspecting object (e.g., tap water) is explained. When key-on operation is performed against the operating key of the switch SW1, the operation signal is provided to the input terminal P7 of the CPU 3 and then the CPU 3 operates in the measurement mode. After the operation of the switch SW1, the head 10 is soaked in the liquid of inspecting object, which is stirred. Then the liquid flows inside the cap 15 soaked in the liquid and the sense part of the sensor electrodes 1a and 1b is soaked in the liquid, so that an electromotive voltage is generated across the sensor electrodes 1a and 1b in response to the chlorine concentration. In this case, the sensor electrode 1a is a positive electrode, and a voltage V1 is generated across the resistor R0 by the electromotive voltage. The voltage V1 as a sense voltage is applied to the non-inverting input end of the operational amplifier OP1 to be amplified without inverting the voltage, and then applied to the input terminal P6 of the CPU 3. The CPU 3 (detection means 31) A/D-converts the sense voltage applied to the input terminal P6 with the built-in A/D conversion part to derive the chlorine concentration through arithmetic, and causes the LCD 4 to display the detection value of the chlorine concentration. Here, since the non-inverting input end and the inverting input end of the operational amplifier OP1 have equal potential, a voltage V2 obtained by dividing the voltage V1 by a combined resistance of the resistor R3 and the resistor(s) R4-R9 is applied to the above another end of the resistor R0. As a result, an impedance value of the impedance element (incl. resistor R0) connected in parallel across the sensor electrodes 1a and 1b is adjusted to a desired value.

Next, the calibration mode for calibrating dispersion in sense voltages is explained. When key-on operation is performed against the operating key of the switch SW2, the operation signal is supplied to the input terminal P8 of the CPU 3 and then the CPU 3 operates in the calibration mode.

In a state that the operational mode of the CPU 3 is changed into the calibration mode, when the head 10 is soaked in water including chlorine of a reference concentration (e.g., 1.5 ppm) and the liquid of inspecting object is stirred, the liquid flows inside the cap 15 soaked in the liquid and the sense part of the sensor electrodes 1a and 1b is soaked in the liquid, so that an electromotive voltage is generated across the sensor electrodes 1a and 1b in response to the chlorine concentration. In this case, the sensor electrode 1a is a positive electrode, and a voltage V1 is generated across the resistor R0 by the electromotive voltage. The voltage V1 is amplified without inverting V1 through the operational amplifier OP1 and then applied to the input terminal P6 of the CPU 3. The CPU 3 A/D-converts the sense voltage applied to the input terminal P6 with the built-in A/D conversion part and then derives the chlorine concentration through arithmetic. The calibration means 32 of the CPU 3 turns on/off switch means 34 using the division ratio setting means 33, and adjusts the division ratio of the voltage divider 2 by selectively connecting the resistor (s) R5-R9 in parallel to the resistor R4. Just then, a voltage V2 applied to the above another end of the resistor R0 is adjusted. Thereby, since an input impedance across the sensor electrodes is changed, the calibration means 32 sets the division ratio of the voltage divider 2 to the division ratio so that the voltage level (i.e., sense voltage V1) of the input terminal P6 substantially agrees with the reference voltage corresponding to the reference concentration. Accordingly, the division ratio controlling means is constructed by the calibration means 32 and the division ratio setting means 33 that are realized by the arithmetic function of the CPU 3, while an impedance adjustment means is constructed from the division ratio controlling means, the resister R0 and the voltage divider 2.

In addition, for a definite period of time from start of operation in the calibration mode (e.g., from 5 seconds elapsed time up to 30 seconds elapsed time), the CPU 3 decreases a combined resistance value of the resistors R4-R9 (i.e., resistance value of the impedance element Z3) to lower the division ratio of the voltage divider 2 per (prescribed) sampling period if the sense voltage V1 is higher than the reference voltage, while the CPU 3 increases the combined resistance value of the resistors R4-R9 to raise the division ratio of the voltage divider 2 per sampling period if the sense voltage V1 is lower than the reference voltage. The CPU 3 stores the smallest combined resistance value of the resistors R4-R9 during the definite period of time as a set value, and applies a divided voltage to the resistor R0 in the succeeding measurement mode. The divided voltage is obtained by dividing by the division ratio decided based on the set value.

Thus, since the voltage divider 2 derives a voltage by dividing an electromotive voltage generated across the sensor electrodes 1a and 1b by the prescribed division ratio and then applies the voltage to the above another end of the resistor R0, it is possible to artificially change the impedance value of the input impedance that is connected between the sensor electrodes 1a and 1b and includes the resistor R0, based on the sense voltage when soaked in the liquid including chlorine of the reference concentration. It is also possible to reduce dispersion in the electromotive voltages generated across the sensor electrodes 1a and 1b and improve sense precision of chlorine concentration.

Figure 5A:
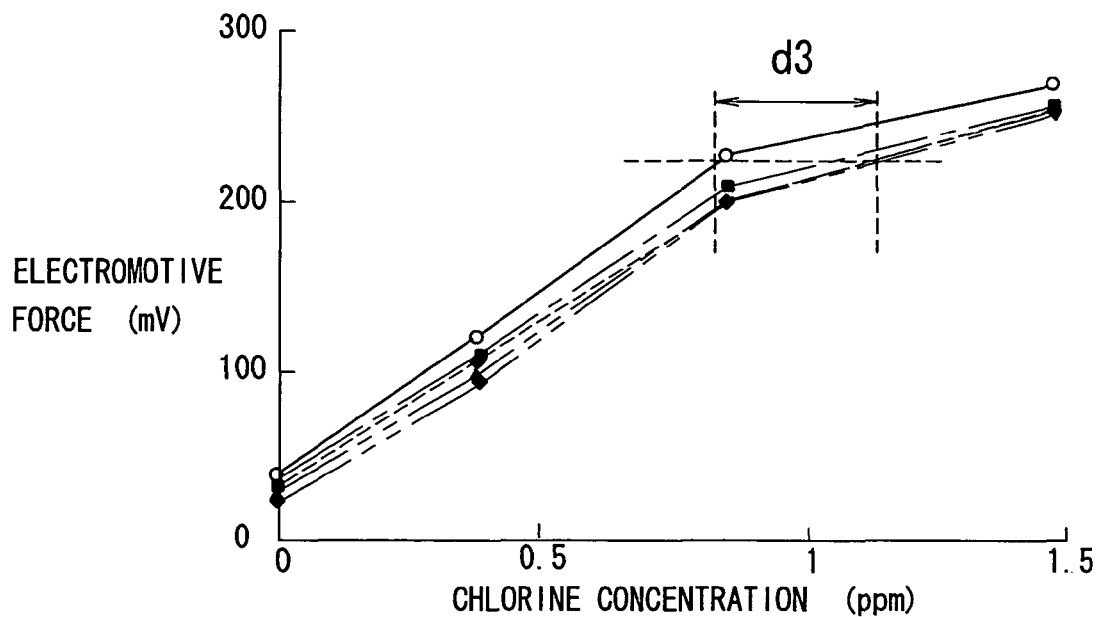
FIG. 5a is a characteristic curve of an output of the above water quality analyzer before calibration of its sense voltage.

FIG. 5a shows a result of the above calibration process with reference to electromotive voltages of sensors that are soaked in a liquid (clean water) with chlorine concentration of 0% and liquids (tap water) with 0.4 ppm (residual chlorine concentration), 0.9 ppm and 1.5 ppm. For example, dispersion d3 of chlorine concentration generating the electromotive voltage of about 220 mV was 0.82-1.13 ppm. It is possible to reduce dispersion in the electromotive voltages as compared with the conventional water quality analyzer and improve measurement precision.

Figure 5B:
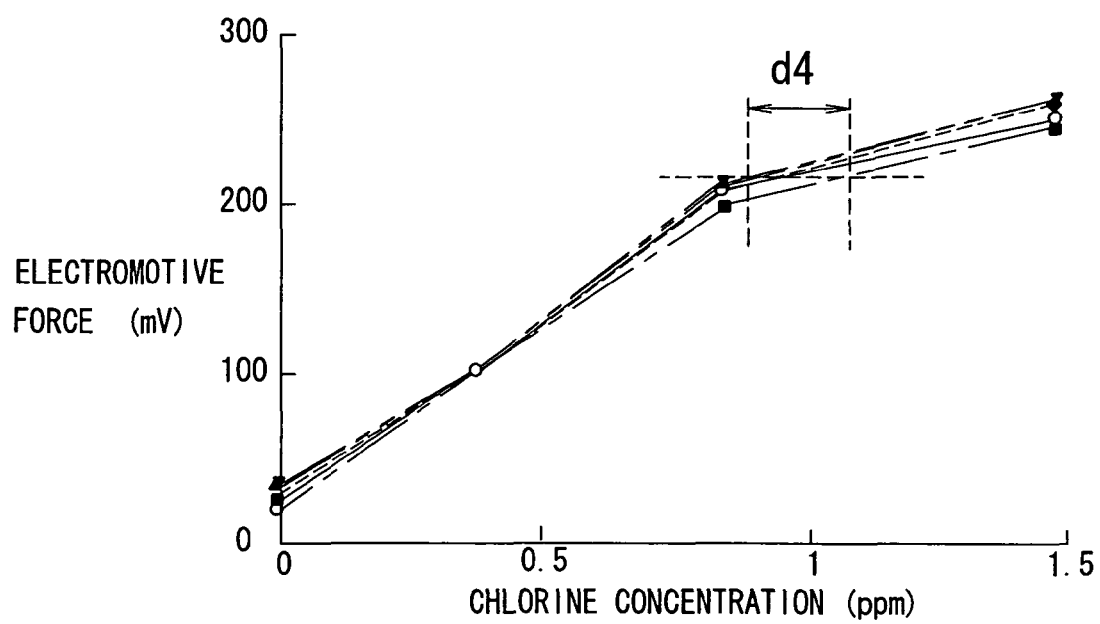
FIG. 5b is a characteristic curve of an output of the above water quality analyzer after calibration of its sense voltage.

After the sense voltage is calibrated by the above method, the CPU 3 may perform a shift calibration. After the above calibration operation is completed, the head 10 is soaked in a liquid including chlorine of a prescribed concentration (e.g., 0.4 ppm), and the liquid of inspecting object is stirred. Then, the liquid flows inside the cap 15 soaked in the liquid and the sense part of the sensor electrodes 1a and 1b is soaked in the liquid, so that an electromotive voltage is generated across the sensor electrodes 1a and 1b in response to the chlorine concentration. A voltage V1 is generated across the resistor R0 by the electromotive voltage. The voltage V1 as a sense voltage is applied to the non-inverting input end of the operational amplifier OP1 to be amplified without inverting V1 and then applied to the input terminal P6 of the CPU 3. Just then, the CPU 3 derives and stores a bias margin for substantially harmonizing a voltage level (i.e., sense voltage) of the input terminal P6 with a reference voltage (e.g., 100 mV) in a prescribed concentration (0.4 ppm). In the succeeding measurement mode, if an electromotive voltage across the sensor electrodes 1a and 1b is shift-calibrated by adding or subtracting the above bias margin to or from the voltage level of the input terminal P6 in region of high concentration side, it is possible to further reduce dispersion in electromotive voltages. FIG. 5b shows a result in case of addition of the shift calibration to the measurement result of FIG. 5a. For example, dispersion d4 of chlorine concentration generating the electromotive voltage of about 220 mV was 0.9-1.1 ppm, and it is possible to further improve measurement precision since the error range can be reduced to ±10%.

Incidentally, the chloride is explained as an example of solute dissolved in the liquid in the above explanation, but the solute is not limited to the chloride, it may be any solute as long as the sensor electrodes 1a and 1b have sensitivity to the solute. For example, in any case that at least one of dissolved ozone, dissolved oxygen, dissolved carbon dioxide and dissolved hydrogen is dissolved as the solute in the liquid, measurement of solute concentration is possible.

Figure 6:
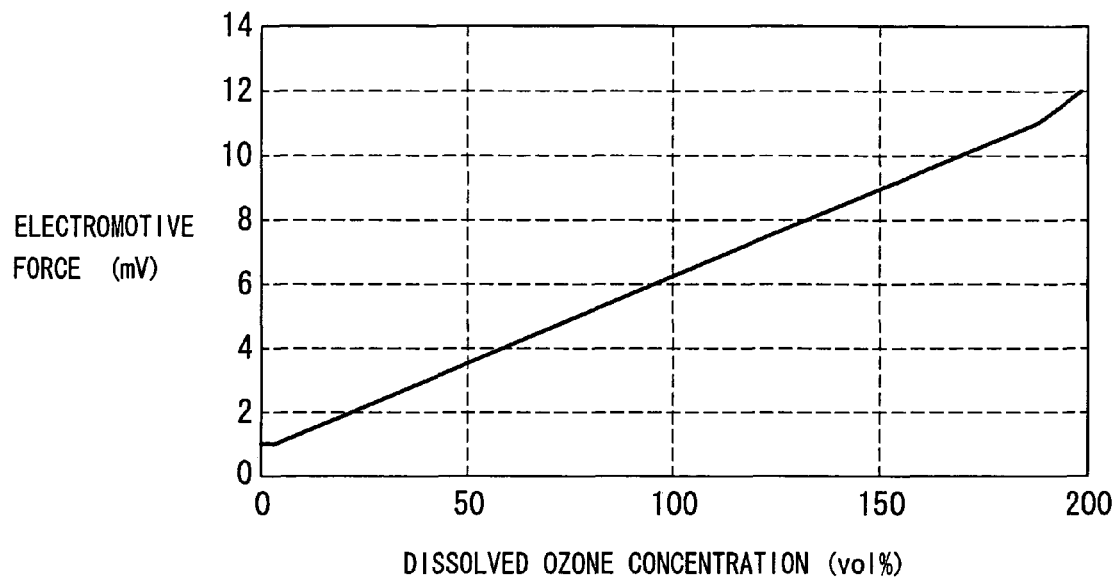
FIG. 6 is a curve showing the relationship between electromotive voltages and concentration of dissolved ozone according to the same as the above.
Figure 7:
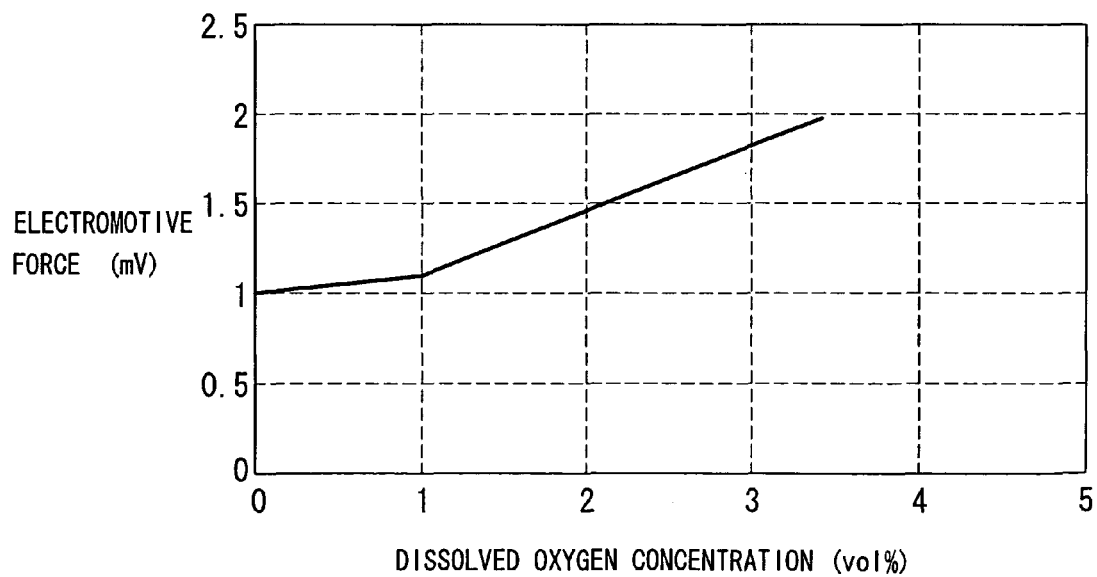
FIG. 7 is a curve showing the relationship between electromotive voltages and concentration of dissolved oxygen according to the same as the above.
Figure 8:
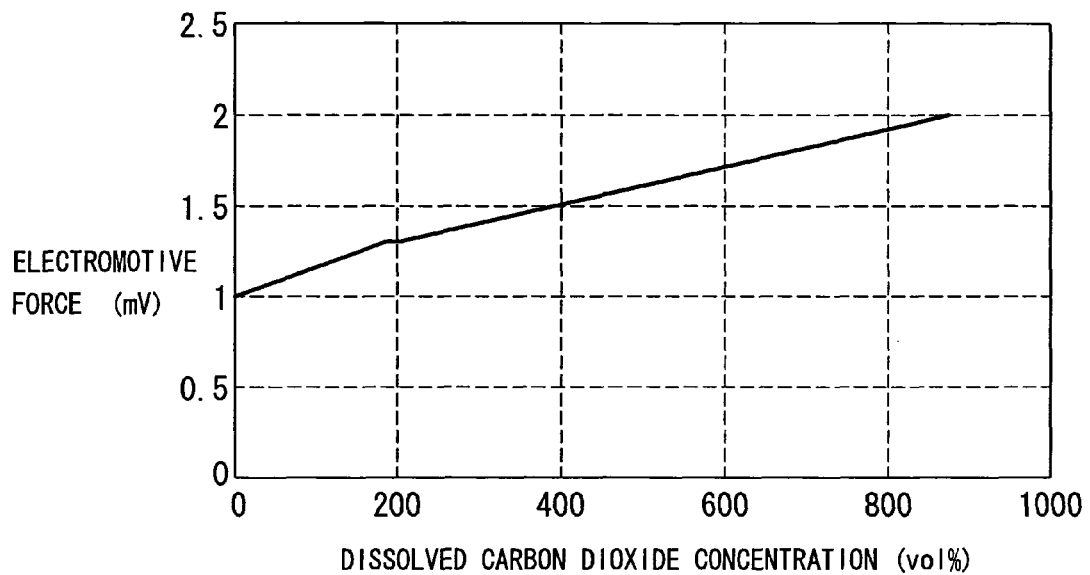
FIG. 8 is a curve showing the relationship between electromotive voltages and concentration of dissolved carbon dioxide according to the same as the above.
Figure 9:
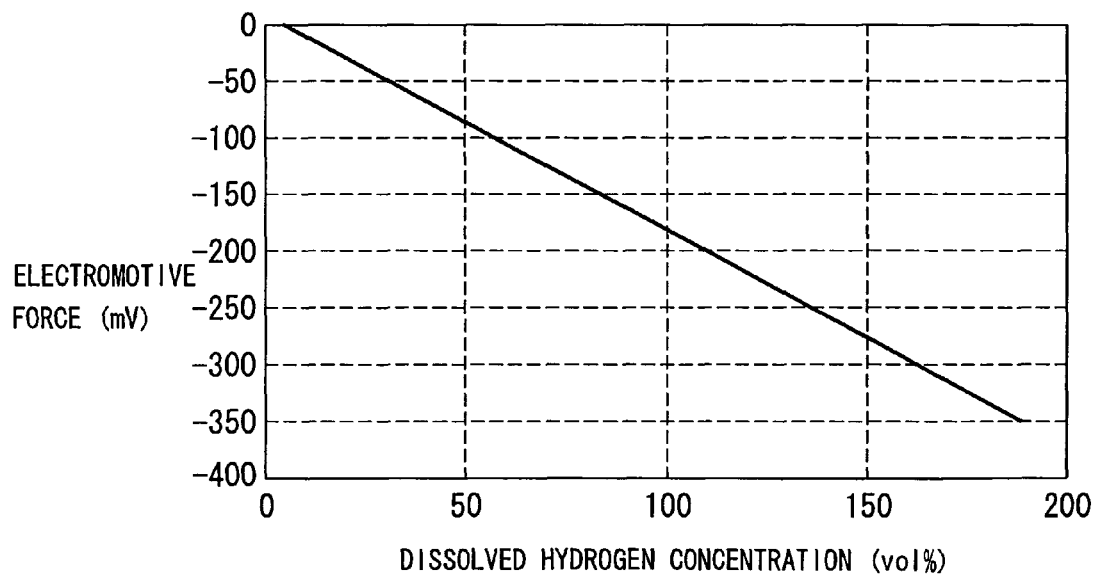
FIG. 9 is a curve showing the relationship between electromotive voltages and concentration of dissolved hydrogen according to the same as the above.

FIG. 6 shows the relationship between electromotive voltages (mV) and concentration (volume percentage) of dissolved ozone, FIG. 7 shows the relationship between electromotive voltages and concentration of dissolved oxygen, FIG. 8 shows the relationship between electromotive voltages and concentration of dissolved carbon dioxide, and FIG. 9 shows the relationship between electromotive voltages and concentration of dissolved hydrogen. There is a substantially proportional relationship between electromotive voltages and concentration of dissolved ozone, dissolved oxygen, dissolved carbon dioxide or dissolved hydrogen as solute. Namely, since the sensor electrodes 1a and 1b have sensitivity to dissolved ozone, dissolved oxygen, dissolved carbon dioxide and dissolved hydrogen in a liquid, concentration of dissolved ozone, dissolved oxygen, dissolved carbon dioxide, dissolved hydrogen can be detected from the both electrodes 1a and 1b. By performing the calibration process in respect to those measuring objects as well as the above, dispersion in electromotive voltages can be reduced and measurement precision can be improved. Incidentally, in case of dissolved hydrogen, a negative voltage is generated.

Second Embodiment

Figure 10:
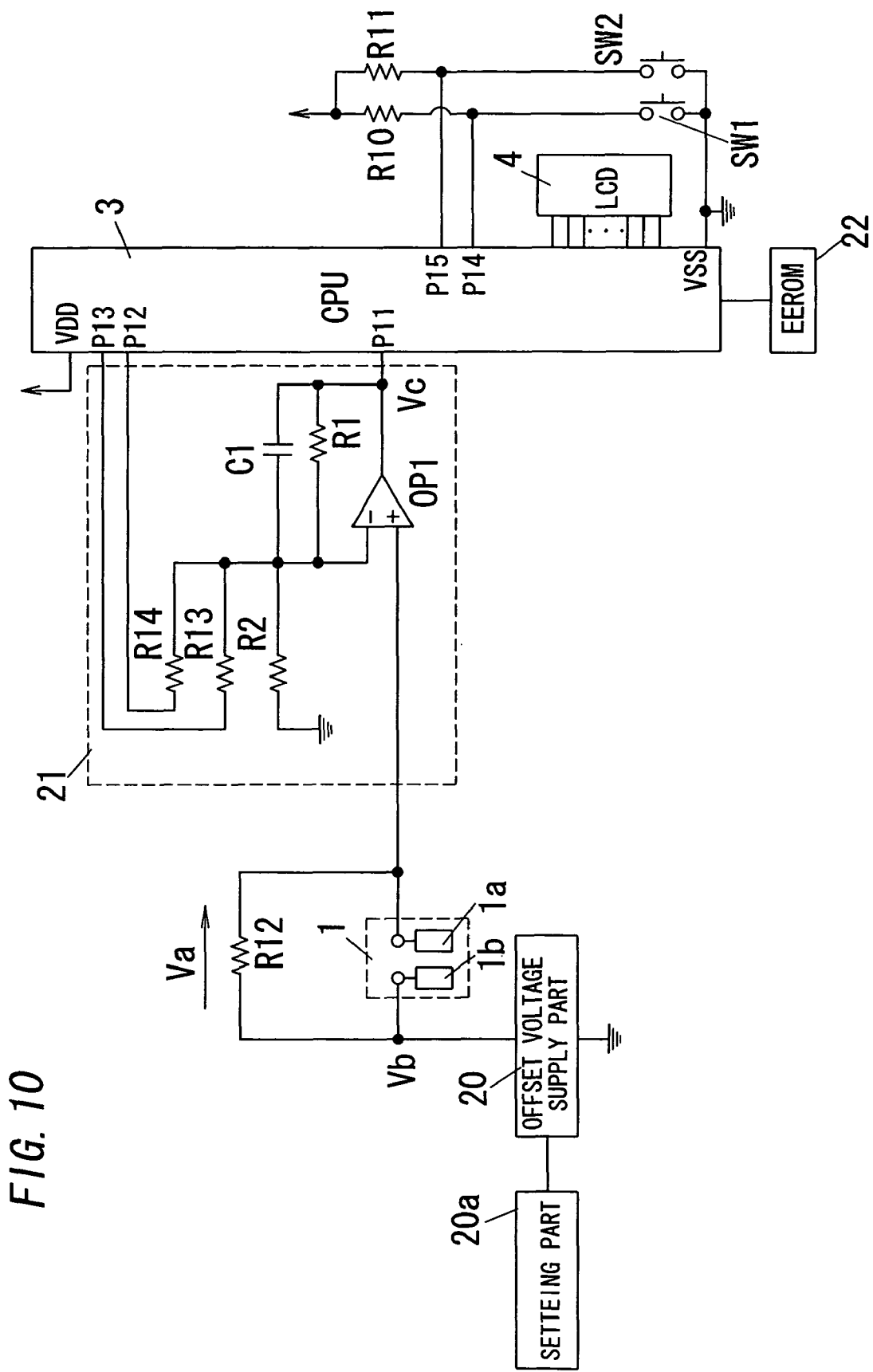
FIG. 10 is a circuit diagram of a water quality analyzer according to a second embodiment of the present invention.
Figure 11:
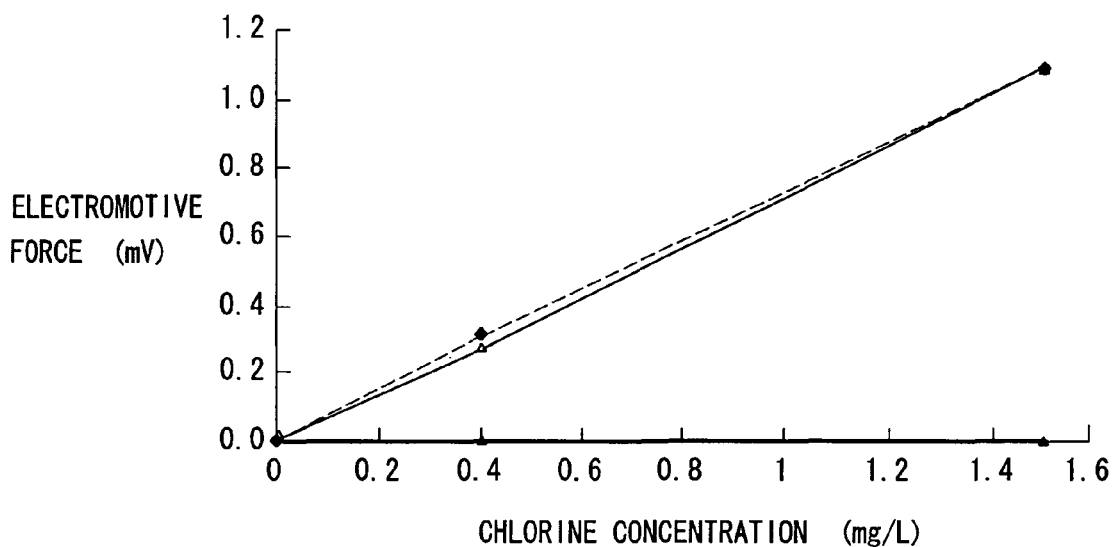
FIG. 11 is a curve showing the relationship between chlorine concentration and electromotive voltages when a resistance value of a correction resistor is 2 kΩ.
Figure 12:
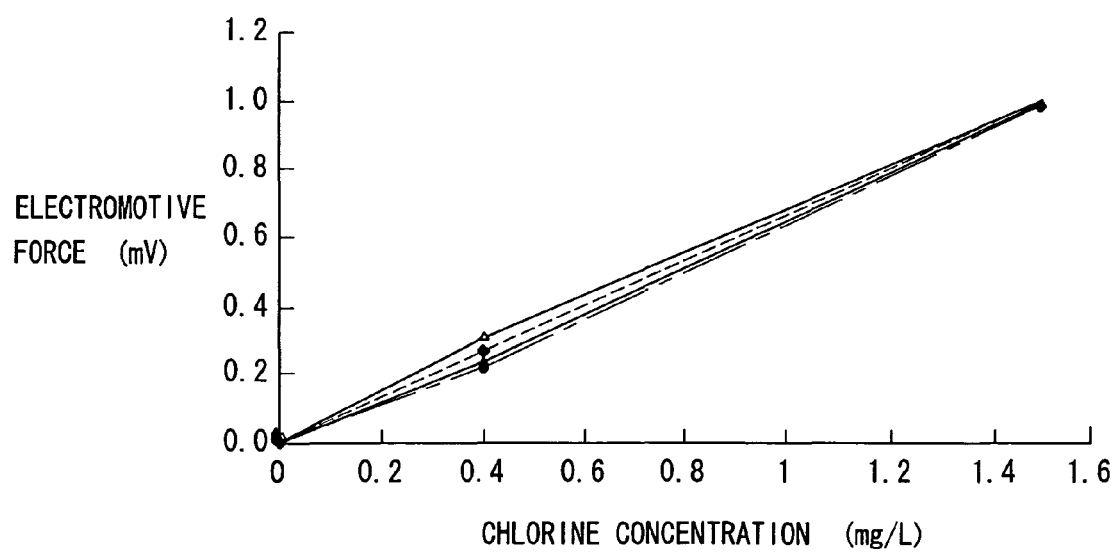
FIG. 12 is a curve showing the relationship between chlorine concentration and electromotive voltages when a resistance value of a correction resistor is 20 kΩ.
Figure 13:
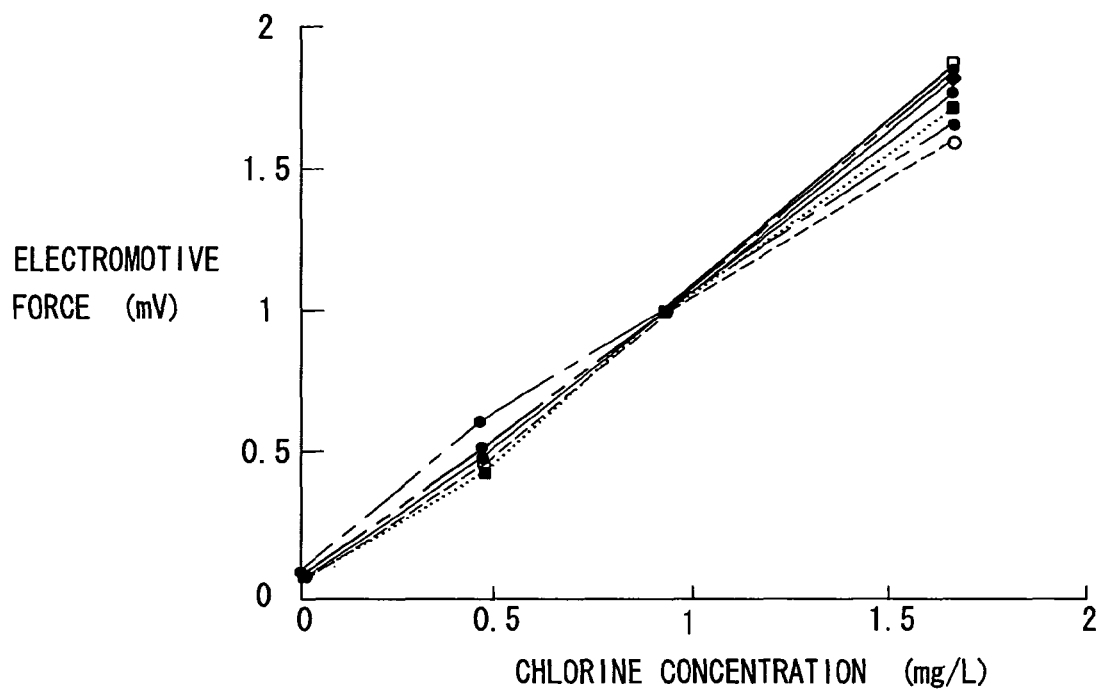
FIG. 13 is a curve showing the relationship between chlorine concentration and electromotive voltages when a resistance value of a correction resistor is 100 kΩ.
Figure 14:
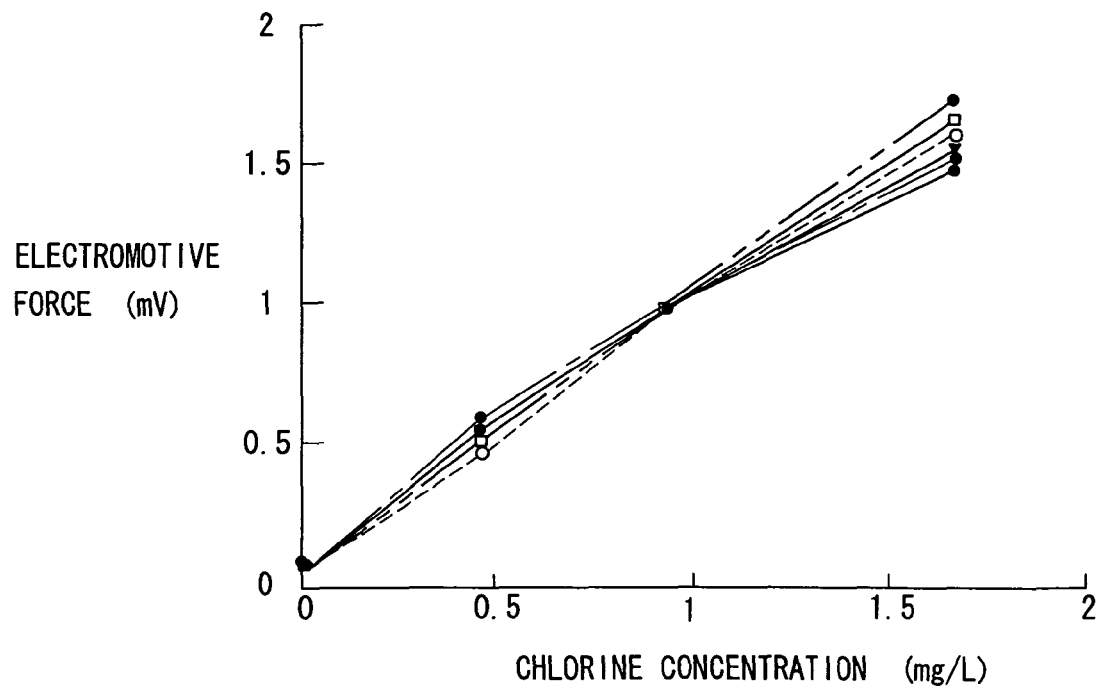
FIG. 14 is a curve showing the relationship between chlorine concentration and electromotive voltages when a resistance value of a correction resistor is 200 kΩ.
Figure 15:
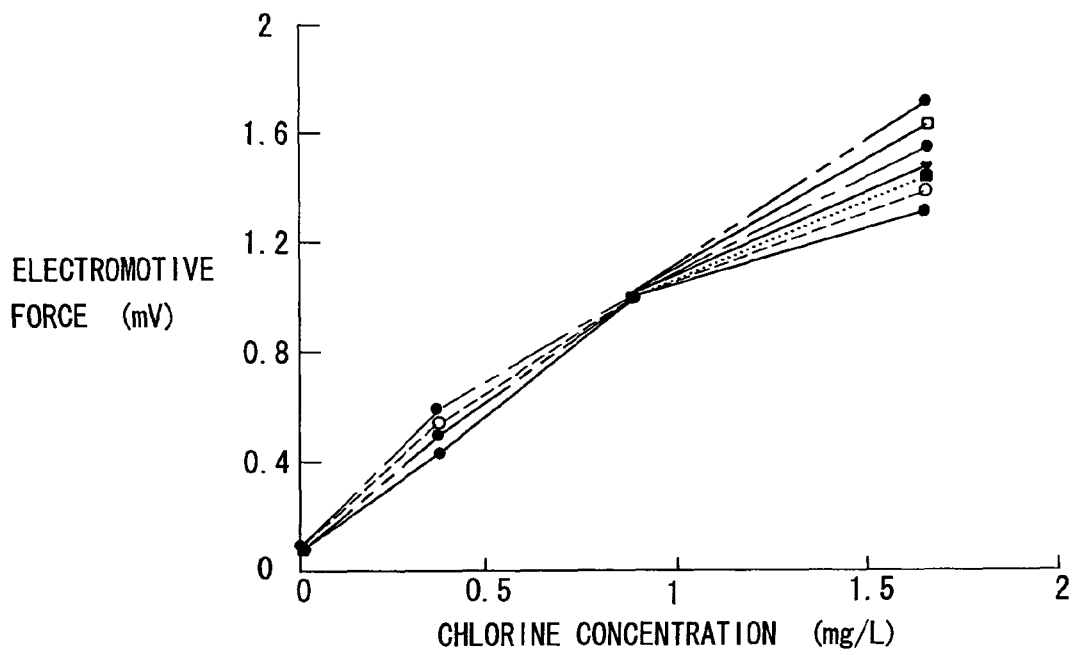
FIG. 15 is a curve showing the relationship between chlorine concentration and electromotive voltages when a resistance value of a correction resistor is 390 kΩ.
Figure 16:
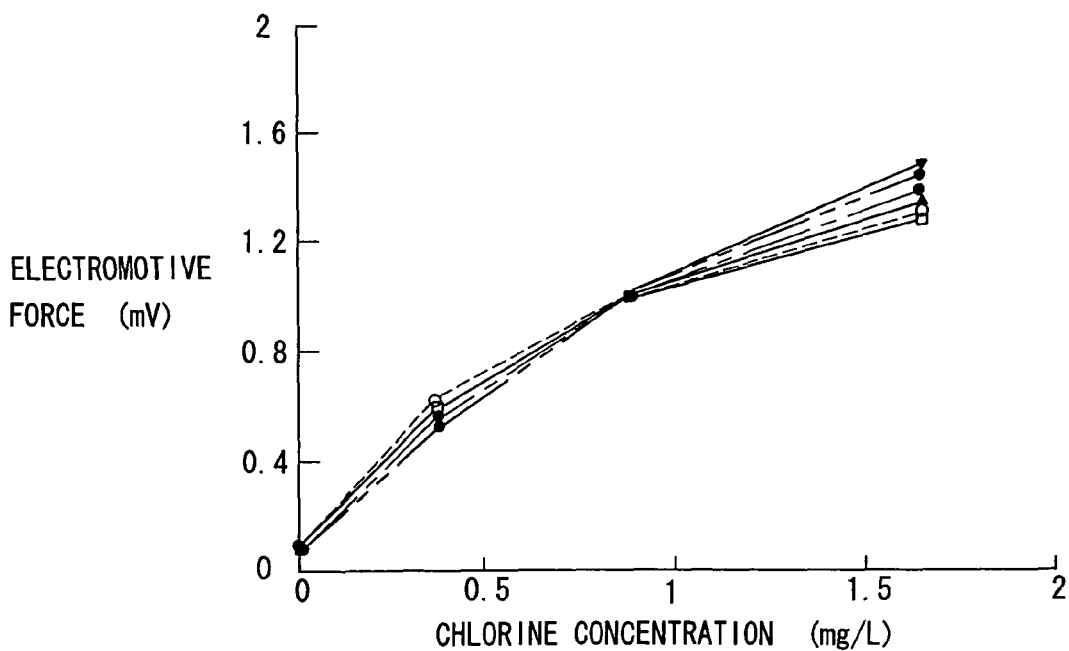
FIG. 16 is a curve showing the relationship between chlorine concentration and electromotive voltages when a resistance value of a correction resistor is 1 MΩ.
Figure 17:
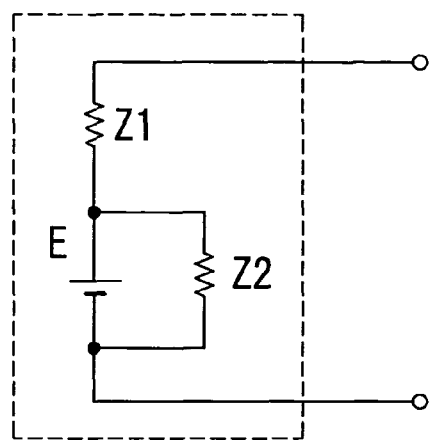
FIG. 17 is an equivalent circuit diagram of a prior art sensor.
Figure 18A:
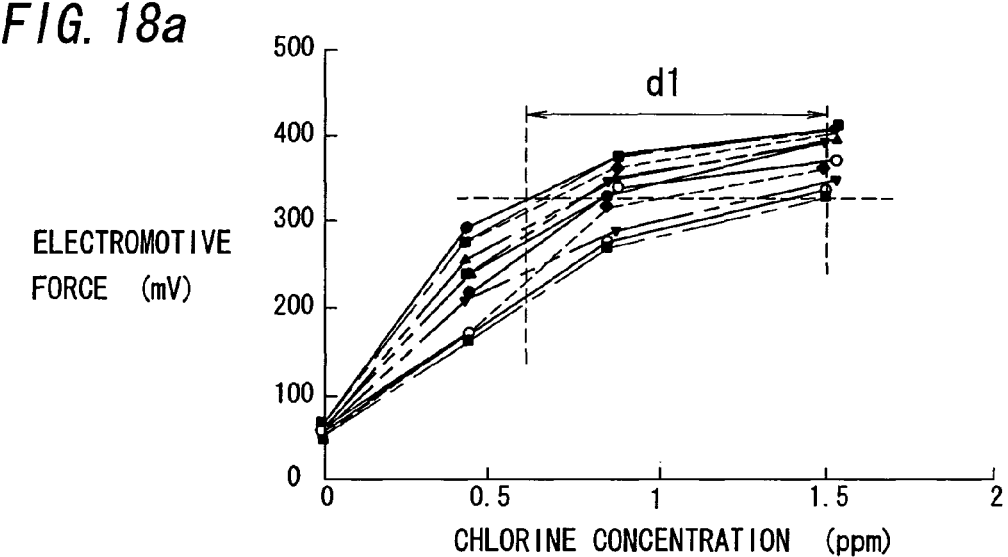
FIG. 18a is an output characteristic curve of a water quality analyzer of a prior art before calibration of its sense voltage.
Figure 18B:
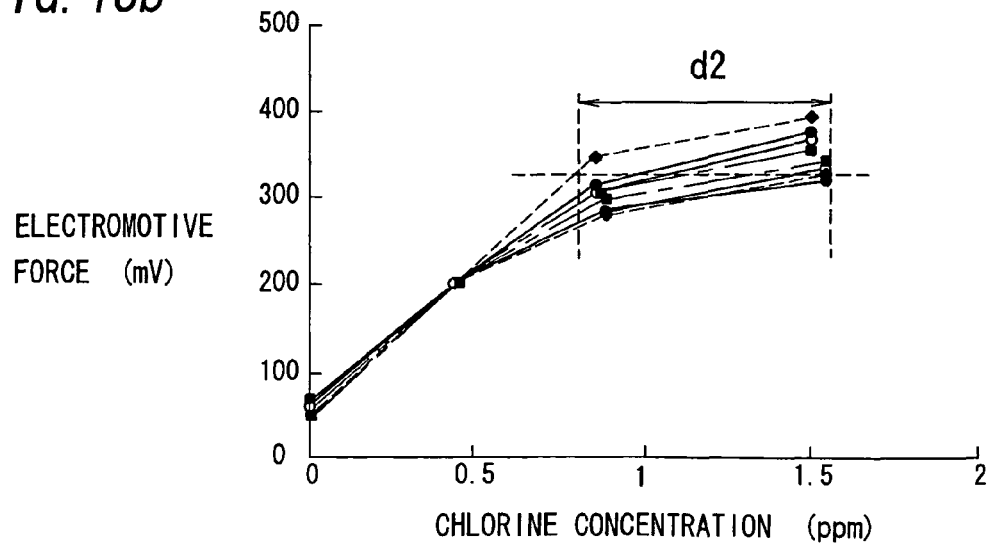
FIG. 18b is an output characteristic curve of a water quality analyzer of a prior art after calibration of its sense voltage.

FIG. 10 shows a water quality analyzer according to a second embodiment of the present invention. Since mechanical construction of the water quality analyzer is similar to that of the first embodiment, like kind constructive elements are assigned the same reference numerals as those in the embodiment, and the description is omitted.

The water quality analyzer comprises a sensor 1, a resistor R12, an offset voltage supply part 20, a setting part 20a, a sense voltage amplification circuit 21, a CPU 3, an EEPROM 22 and a LCD 4. The sensor 1 is comprised of a pair of sensor electrodes 1a and 1b that are made of different metals from each other. When soaked in a liquid of inspecting object, the sensor electrodes generate a sense voltage Va in proportion to concentration of impurities in the liquid. The resistor 12 as an impedance element is connected between the sensor electrodes 1a and 1b in order to improve non-linearity of the sense voltage Va. The offset voltage supply part 20 superposes an offset voltage Vb on the sense voltage Va across the sensor electrodes 1a and 1b. The setting part 20a alternatively selects the offset voltage Vb superposed through the offset voltage supply part 20 among voltage values. The sense voltage amplification circuit 21 amplifies the sense voltage (Va+Vb) on which the offset voltage Vb is superposed.

The sense voltage amplification circuit 21 is comprised of a non-inverting amplification circuit using an operational amplifier OP1, whose non-inverting input terminal is connected with the sensor electrode 1a of the positive side in the sensor electrodes 1a and 1b. A parallel circuit comprised of a resistor R1 and a condenser C1 for adjusting response is connected between an output end and an inverting input end of the operational amplifier OP1, while a resistor R2 is connected between the inverting input end of the operational amplifier OP1 and a circuit ground. One ends of resistors R13 and R14 for adjusting gain are connected to the inverting input end of the operational amplifier OP1, and also another ends of the resistors R13 and R14 are connected to output terminals P12 and P13 of the CPU 3, respectively. The output end of the operational amplifier OP1 is connected to an input terminal P11 of the CPU 3.

Here, the output terminals P12 and P13 of the CPU 3 are open collector outputs, and the resistors R13 and R14 are connected in parallel with the resistor R2 when the output terminals P12 and P13 are connected to ground. Since the gain of the operational amplifier OP1 is decided by a resistance ratio of the resistors R2, R13 and R14 connected between the inverting input end and ground, and the resistor R1 connected between the inverting input end and the output end, the gain of the operational amplifier OP1 can be changed in 4 ways by opening or closing the output terminals P12 and P13 through the CPU 3.

The EEPROM 22 stores the offset voltage value Vb set with the setting part 20a and the gain of the sense voltage amplification circuit 21 in case of output calibration. In the embodiment, a storage part is the EEPROM, but may be any memory of nonvolatile memories, and also may be a RAM(s) if a backup power source is provided.

The sense voltage Vc amplified with the operational amplifier OP1 is applied to the input terminal P11 of the CPU 3. Chlorine concentration is derived by A/D converting the input voltage Vc with a built-in A/D conversion part and then a detection value of the chlorine concentration is displayed on the LCD 4.

An operation signal through a switch SW1 for measurement start is supplied to an input terminal P14 of the CPU 3, while an operation signal through a switch SW2 for calibration start is supplied to its input terminal P15. One ends of the switches SW1 and SW2 are connected to ground, and also their another ends are pulled up to a constant voltage through resistors R10 and R11, respectively. Accordingly, if a voltage level of the input terminal P14 or P15 is set to Low or High by turning on/off the switch SW1 or SW2 and then an operation signal is supplied to the CPU 3, the CPU 3 starts to operate in a measurement mode or a calibration mode.

The operation of the water quality analyzer of the embodiment is now explained.

First, the measurement mode for measuring chlorine concentration in a liquid of inspecting object (e.g., tap water) is explained. When key-on operation is performed against the operating key 8a of the switch SW1, the operation signal is supplied to the input terminal P14 of the CPU 3 and then the CPU 3 operates in the measurement mode. After the operation of the switch SW1, the head 10a is soaked in the liquid of inspecting object, which is stirred, and then the liquid flows inside the cap 15 soaked in the liquid. Just then, the sense part of the sensor electrodes 1a and 1b is soaked in the liquid, so that an electromotive voltage is generated across the sensor electrodes 1a and 1b in response to the chlorine concentration. In this case, the sensor electrode 1a is a positive electrode, and a voltage Va is generated across the resistor R12 by the electromotive voltage. The offset voltage Vb is superposed on the voltage Va through the offset voltage supply part 20. The superposed voltage (Va+Vb) is amplified without inverting the voltage at a prescribed gain G through the operational amplifier OP1, and then the amplified voltage Vc is applied to the input terminal P11 of the CPU 3. Just then, the CPU 3 A/D-converts the voltage signal Vc applied to the input terminal P11 with the built-in A/D conversion part to derive the chlorine concentration in the liquid from the voltage signal Vc through arithmetic, and causes the LCD 4 to display an arithmetic result of the chlorine concentration.

FIG. 11-16 show electromotive voltages of sensors that are soaked in a liquid (clean water) with chlorine concentration of 0% and liquids (tap water) with 0.4 ppm (residual chlorine concentration), 0.9 ppm and 1.5 ppm when a resistance value of the resistor R12 is 2 k$\Omega$, 20 k$\Omega$, 100 k$\Omega$, 200 k$\Omega$, 390 k$\Omega$ and 1 M$\Omega$, respectively. From these measurement results, it is understood that linearity of sense voltages can be improved as compared with the conventional water quality analyzer. Incidentally, if a resistance value of the resistor R12 connected between the sensor electrodes 1a and 1b is too small, a current flowing between the sensor electrodes 1a and 1b is increased to shorten the life time of the electrodes and also an electromotive voltage generated across the sensor electrodes 1a and 1b becomes small. As a result, since a costly element with high resolution must be used for the operational amplifier OP1, the resistance value of the resistor R12 is preferably equal to or more than 1 k$\Omega$. The linearity is improved as compared with no resistor R12, but there is a tendency that the linearity of sense voltages is deteriorated as the resistance value of the resistor R12 is increased. Accordingly, the resistance value of the resistor R12 is preferably equal to or less than 1 M$\Omega$.

Next, the calibration mode for calibrating a detection value of chlorine concentration is explained. When key-on operation is performed against the operating key 8b of the switch SW2, the operation signal is supplied to the input terminal P15 of the CPU 3 and then the CPU 3 operates in the calibration mode of the offset voltage Vb. After the operation of the switch SW2, the head 10a is soaked in clean water (i.e., test liquid with impurity concentration of 0%), which is stirred. Then the liquid flows inside the cap 15 soaked in the liquid and the sense part of the sensor electrodes 1a and 1b is soaked in the liquid, so that an electromotive voltage is generated across the sensor electrodes 1a and 1b in response to the chlorine concentration. The CPU 3 derives the chlorine concentration through arithmetic based on the sense voltage and then causes the LCD 4 to display it. In this case, user's operation is performed against the setting part 20a while checking the display on the LCD 4 and thereby the offset voltage Vb is adjusted so that the display on the LCD 4 becomes 0. After the adjustment, the CPU 3 derives the offset voltage Vb from the voltage Vc applied to the input terminal P11 when the sensor electrodes 1a and 1b are took out from the liquid, and then stores the offset voltage Vb in the EEPROM 22. Incidentally, an operating button of the setting part 20a is not shown in FIG. 2, but it is located on the surface of the housing 5.

After the calibration of the offset voltage Vb is completed, the mode is shifted to a calibration mode of gain through follow-up operation of the operating key 8b or the like. Just then, the head 10a is soaked in a liquid including chlorine of a prescribed reference concentration (e.g., 1.5 ppm) and the liquid of inspecting object is stirred. Then, the liquid flows inside the cap 15 soaked in the liquid and the sense part of the sensor electrodes 1a and 1b is soaked in the liquid, so that an electromotive voltage is generated across the sensor electrodes 1a and 1b in response to the chlorine concentration. In this case, the sensor electrode 1a is a positive electrode, and a voltage Va is generated across the resistor R12 by the electromotive voltage, on which the offset voltage Vb is superposed through the offset voltage supply part 20. The superposed voltage signal (Va+Vb) is amplified without inverting the voltage through the operational amplifier OP1, and then is applied to the input terminal P11 of the CPU 3. The CPU 3 A/D-converts the voltage signal Vc applied to the input terminal P11 with the built-in A/D conversion part to calculate the chlorine concentration from the voltage signal Vc, and then causes the LCD 4 to display the calculated result. The CPU 3 changes the gain G of the operational amplifier OP1 by opening or closing the output terminals P12 and P13, and sets the gain G of the operational amplifier OP1 to the gain by which the calculated result of the chlorine concentration most approximates the chlorine concentration (e.g., 1.5 ppm) of the test liquid. When the calibration process of gain is completed, the CPU 3 stores the set gain G in the EEPROM 22.

Thus, the calibration of output is performed, and the offset voltage Vb and the gain G set in the calibration are stored in the EEPROM 22. In succeeding measurement, the CPU 3 reads out the offset voltage Vb and the gain G from the EEPROM 22, and sets the offset value at the offset voltage supply part 20 and the gain of the sense voltage amplification circuit 21 to the values stored in the EEPROM. Accordingly, it is possible to easily cope with the case of setting change of the offset voltage Vb and the gain G, and circuit construction can be simplified.

Incidentally, the chloride is explained as an example of solute dissolved in the liquid in the above explanation, but the solute is not limited to the chloride, the present invention is applicable to every solute which the sensor electrodes 1a and 1b have sensitivity to. For example, as described in the first embodiment, the sensor electrodes 1a and 1b have sensitivity to dissolved ozone, dissolved oxygen, dissolved carbon dioxide and dissolved hydrogen, and therefore solute concentration can be detected from an electromotive voltage across the sensor electrodes 1a and 1b in any case that at least one of dissolved ozone, dissolved oxygen, dissolved carbon dioxide and dissolved hydrogen is dissolved in the liquid as the solute. With respect to those measuring objects, linearity of sense voltages can be improved by connecting the resistor R12 having a prescribed resistance value between the sensor electrodes 1a and 1b as well as the above. It is also possible to perform the calibration process as well as the above.

Thus, as many apparently widely different embodiments of this invention may be made without departing from the spirit and scope thereof, it is to be understood that the invention is not limited to the specific embodiments thereof except as defined in the appended claims.

The invention claimed is:

1. A water quality analyzer, comprising:
a pair of sensor electrodes that are made of different metals from each other and are soaked in water and used, the sensor electrodes generating a sense voltage across the electrodes in proportion to concentration of impurities included in the water;
a detection means that detects concentration of solute from a voltage value of the sense voltage to provide a detection result;
an impedance element that is connected between the sensor electrodes to improve non-linearity of the sense voltage;
an offset voltage supply means that superposes an offset voltage on the sense voltage; and
a setting means that changes said offset voltage of said offset voltage supply means and detection sensitivity of said detection means.

2. The water quality analyzer of claim 1, wherein said detection means comprises an amplification means that amplifies at a prescribed gain a voltage obtained by the sense voltage and the offset voltage superposed on the sense voltage, wherein the above detection means detects the concentration of solute based on a voltage value of an output voltage of the amplification means, wherein
said setting means provides a calibration mode of the sense voltage, and sets the offset voltage and the gain so that with the sensor electrodes soaked in a liquid of reference concentration, the sense voltage generated across the sensor electrodes agrees with a reference voltage corresponding to the above reference concentration in the calibration mode.

3. The water quality analyzer of claim 1 or 2, wherein the impedance value of the impedance element is equal to or more than 1 k$\Omega$ and equal to or less than 1 M$\Omega$.

4. The water quality analyzer of claim 1, further comprising memory means to store the offset voltage and the gain obtained at the calibration mode.

5. The water quality analyzer of claim 4, wherein said memory means comprises a RAM with a backup power source.

6. The water quality analyzer of claim 4, wherein said memory means comprises a nonvolatile memory.

7. The water quality analyzer of claim 6, wherein said nonvolatile memory comprises an EEPROM.

8. A water quality analyzer, comprising:
a pair of sensor electrodes that are made of different metals from each other and are soaked in water and used, the sensor electrodes generating a sense voltage across the electrodes in proportion to concentration of impurities included in the water;
a detection means that detects concentration of solute from a voltage value of the sense voltage to provide a detection result;
an impedance element that is connected between the sensor electrodes, and having an impedance value which is a resistance value that can improve non-linearity of the sense voltage;
an offset voltage supply means that superposes an offset voltage on the sense voltage; and
an amplification means that amplifies a voltage obtained by superposing the offset voltage on the sense voltage at a prescribed gain to provide for the detection means, wherein the above detection means detects the concentration of solute based on a voltage value of an input voltage from the amplification means; and
a setting means that provides a calibration mode of the sense voltage and sets the offset voltage and the gain so that with the sensor electrodes soaked in a liquid of reference concentration, the sense voltage generated across the sensor electrodes agrees with a reference voltage corresponding to the above reference concentration in the calibration mode.

9. The water quality analyzer of claim 8, wherein the impedance value of the impedance element is equal to or more than 1 k$\Omega$ and equal to or less than 1 M$\Omega$.

* * * * *